United States Patent
Wood

(10) Patent No.: US 6,827,913 B2
(45) Date of Patent: Dec. 7, 2004

(54) MODULAR STERILIZATION TRAY SYSTEMS FOR MEDICAL INSTRUMENTS

(75) Inventor: Timothy E. Wood, Weare, NH (US)

(73) Assignee: Symmetry Medical, Inc., Warsaw, IN (US)

( * ) Notice: Subject to any disclaimer, the term of this patent is extended or adjusted under 35 U.S.C. 154(b) by 483 days.

(21) Appl. No.: 10/061,749

(22) Filed: Feb. 1, 2002

(65) Prior Publication Data

US 2002/0071799 A1 Jun. 13, 2002

Related U.S. Application Data

(63) Continuation of application No. 09/312,125, filed on May 14, 1999, now abandoned.

(51) Int. Cl.$^7$ .............................................. A61L 2/00
(52) U.S. Cl. .................. 422/300; 206/370; 206/438; 220/505; 220/676; 422/297
(58) Field of Search ................. 422/300, 297; 206/370, 438; 220/676, 505

(56) References Cited

U.S. PATENT DOCUMENTS

| | | | |
|---|---|---|---|
| 4,627,542 A | 12/1986 | Fredrickson | 211/150 |
| 4,643,303 A | 2/1987 | Arp et al. | 206/363 |
| 4,671,943 A | 6/1987 | Wahlquist | 422/300 |
| 4,798,292 A | 1/1989 | Hauze | 206/439 |
| 4,959,199 A | 9/1990 | Brewer | 422/300 |
| 5,174,453 A | 12/1992 | Stoeffler | 422/300 |
| 5,279,800 A | 1/1994 | Berry, Jr. | 422/300 |
| 5,281,400 A | 1/1994 | Berry, Jr. | 422/295 |
| 5,384,103 A | 1/1995 | Miller | 422/310 |
| 5,424,048 A | 6/1995 | Riley | 422/300 |
| 5,441,707 A | 8/1995 | Lewis et al. | 422/300 |
| 5,441,709 A | 8/1995 | Berry, Jr. | 422/297 |
| 5,882,612 A | 3/1999 | Riley | 422/300 |
| 6,331,280 B1 * | 12/2001 | Wood | 422/300 |

* cited by examiner

Primary Examiner—Krisanne Jastrzab
(74) Attorney, Agent, or Firm—Taylor & Aust, P.C.

(57) ABSTRACT

A sterilization tray system which comprises an outer box-like case having holes in the case bottom wall through which steam or other sterilant may circulate through the case. Pairs of brackets are affixed vertically to opposite the case side and/or end walls. A plurality of spaced holes is provided in each bracket. The holes serve as anchoring points for shelf brackets or fixtures for supporting trays at selected positions in the case.

12 Claims, 7 Drawing Sheets

MODULAR STERILIZATION TRAY SYSTEMS FOR MEDICAL INSTRUMENTS

This is a continuation of application Ser. No. 09/312,125, filed May 14, 1999, now abandoned.

This invention relates to the sterilizing of medical instruments and materials. It relates more particular to an improved tray systems to facilitate sterilizing, delivering and presenting surgical instruments and materials in a sterile condition prior to surgery and to preventing contamination from said instruments following surgery.

BACKGROUND OF THE INVENTION

It is normal procedure to provide appropriate types and quantities of surgical instruments and materials for a specific surgical procedure as a sterilized unitary package. Prior to or during an operation, the instruments and materials are removed from the package and laid out on a so-called Mayo table or other surface so that they are readily accessible to the surgeon performing the operation.

A typical instrument package may include a basket or tray in which the instruments are placed. Fixating means such as a finger mat, post or fixture may be provided to fix the positions of the instruments in the basket or tray so that the instruments do not become co-mingled or damaged when the basket or tray is moved about.

As shown in U.S. Pat. Nos. 4,643,303, 4,671,943, and 4,798,292, the basket or tray may be a rigid box-like container with a removable cover to protectively enclose the instruments. Also, in some cases, fixation modules are provided to segregate and fix the positions of the instruments; see, for example, U.S. Pat. No. 4,643,303. Invariably, however, there is little flexibility in the placement of those modules within the container and only a single layer of trays is allowed in the container. This limits the number and variety of instruments that may be sterilized in the container at one time.

The foregoing discussion of the prior art derives in large part from U.S. Pat. No. 5,424,048 in which there is proposed a sterilization tray system comprising an outer box-like case having columns of holes in the case side and end walls as well as the case bottom and top walls through which steam or other sterilant may circulate both vertically and laterally through the case. The holes in the bottom, side and end walls also serve as anchoring points for a variety of different brackets and fixtures for retaining various instruments and instrument trays within the case. According to the '048 patent, the positions of the columns of holes in the opposed side and/or end walls are directly related to the dimensions of the trays to enable the trays to be retained at different positions and elevations within the case.

As described in the '048 patent, the brackets or fixtures are provided with integral posts which extend through the holes provided in the case side and end walls, and/or the tray bottom walls and are locked thereto by means of locking rings. The '048 patent also describes fastening certain of the fixtures to the tray bottom walls by means of threaded fasteners. In its commercial embodiment, the modular sterilization tray system made in accordance with the '048 patent is believed to employ threaded fasteners for mounting the brackets and fixtures to the case. As will be appreciated, the use of threaded fasteners and/or locking rings slows assembly/disassembly, and requires increased inventory of parts which may be lost or misplaced. Additionally, threaded fasteners and/or locking rings are prone to loosening and/or may harbor contamination.

Accordingly, it is an object of the present invention to provide an improved sterilization tray system for medical instruments which overcomes the aforesaid and other problems of the prior art.

Another object is to provide an improved sterilization tray system capable of holding one or more instrument trays arranged in a variety of different positions at elevations within the case and/or a variety of different size instrument trays.

The foregoing and other objects of the invention are achieved by a novel and improved sterilization tray system comprising an outer box-like case having holes in the case bottom walls through which steam or other sterilant may circulate through the case. Pairs of brackets are mounted vertically opposite one another to the case side and/or end walls. A plurality of spaced holes is provided in each bracket. The holes serve as anchoring points for shelf brackets or fixtures for supporting trays at selected positions within the case.

BRIEF DESCRIPTION OF THE DRAWINGS

For a fuller understanding of the nature and objects of the present invention, reference should be made to the following detailed description, taken in connection with the accompanying drawings in which like numerals depict like parts, and wherein.

DETAILED DESCRIPTION OF PREFERRED EMBODIMENT

Figure 1:
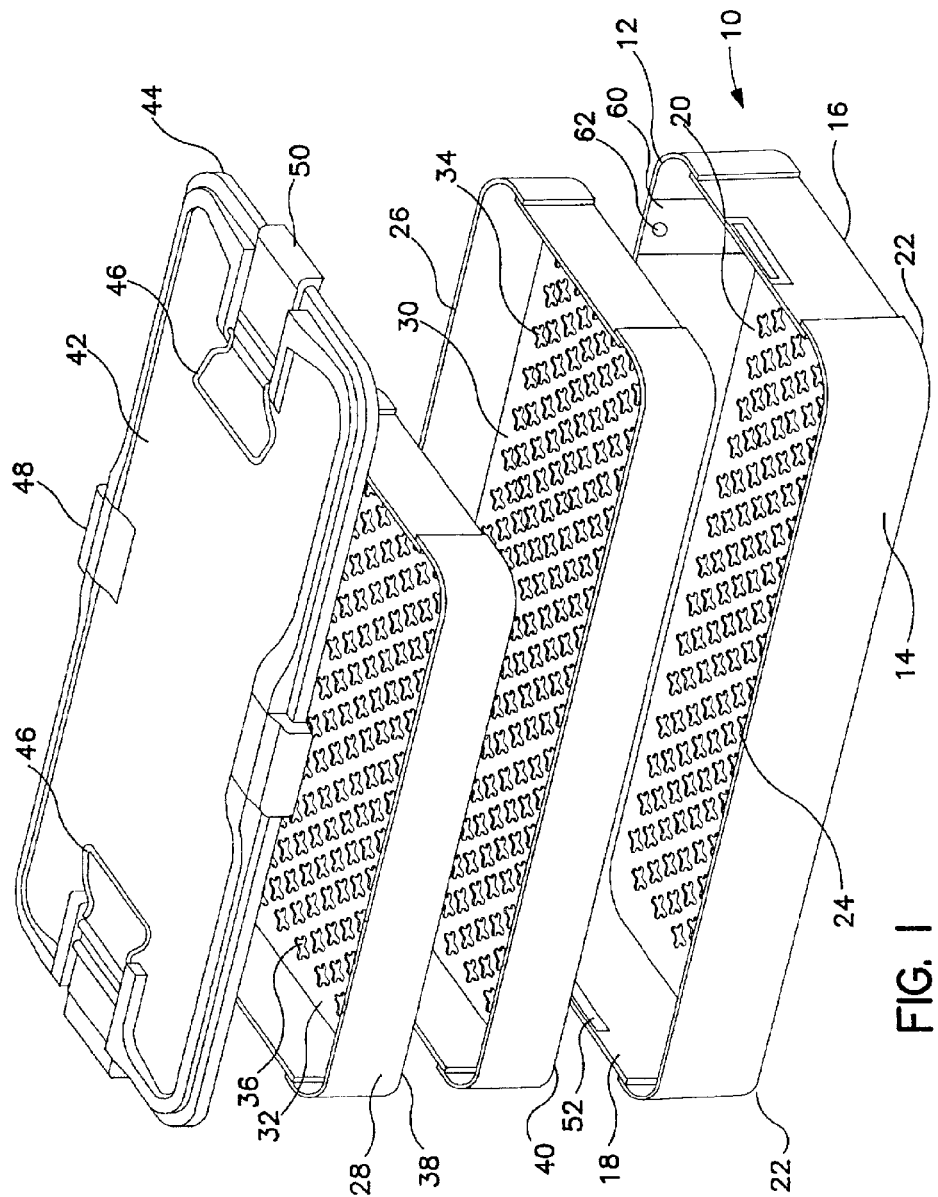
FIG. 1 is an exploded perspective view of a sterilization tray system made in accordance with the present invention.
Figure 2:
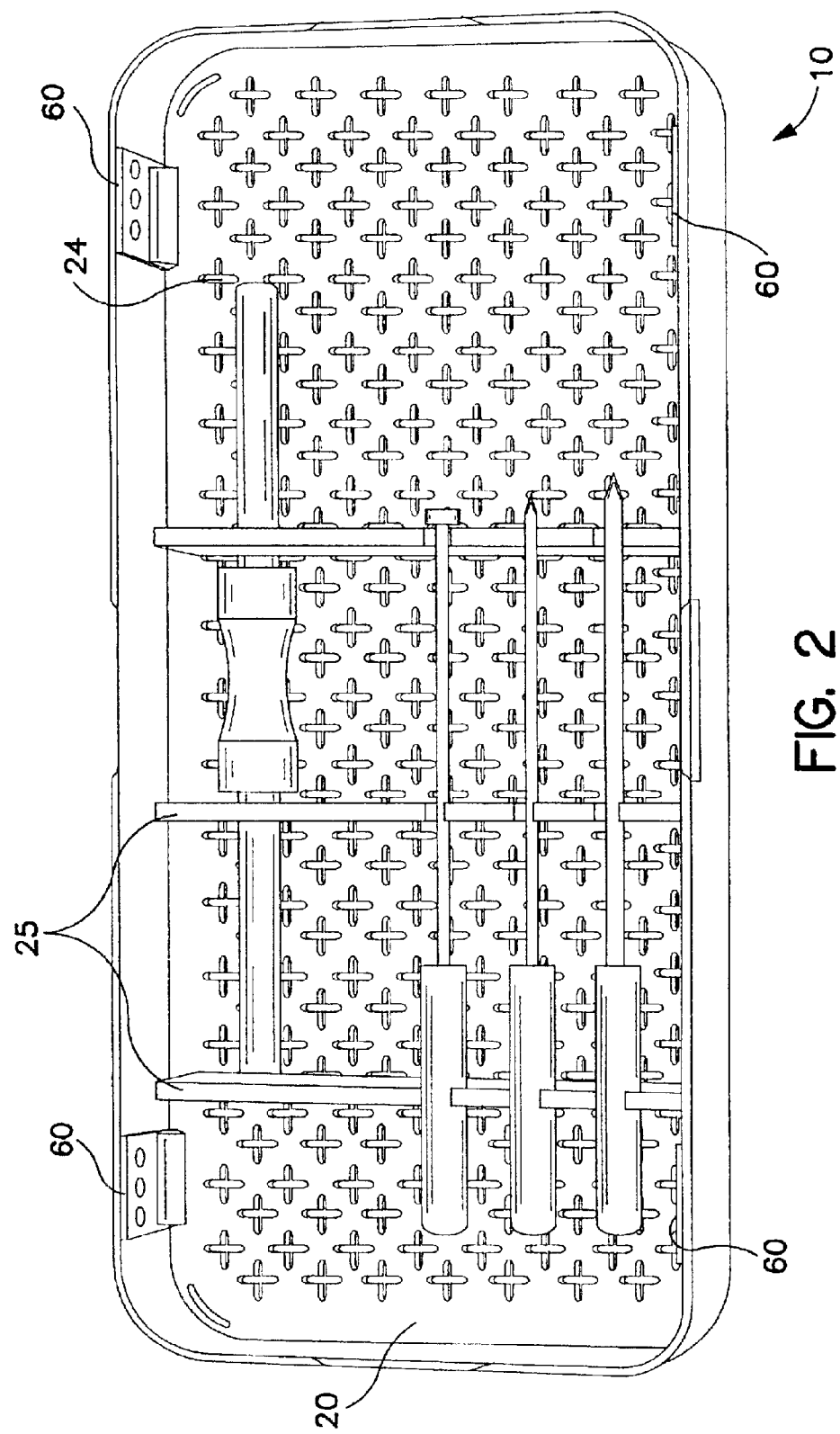
FIG. 2 is a top perspective view of the sterilization tray system of the present invention.
Figure 3:
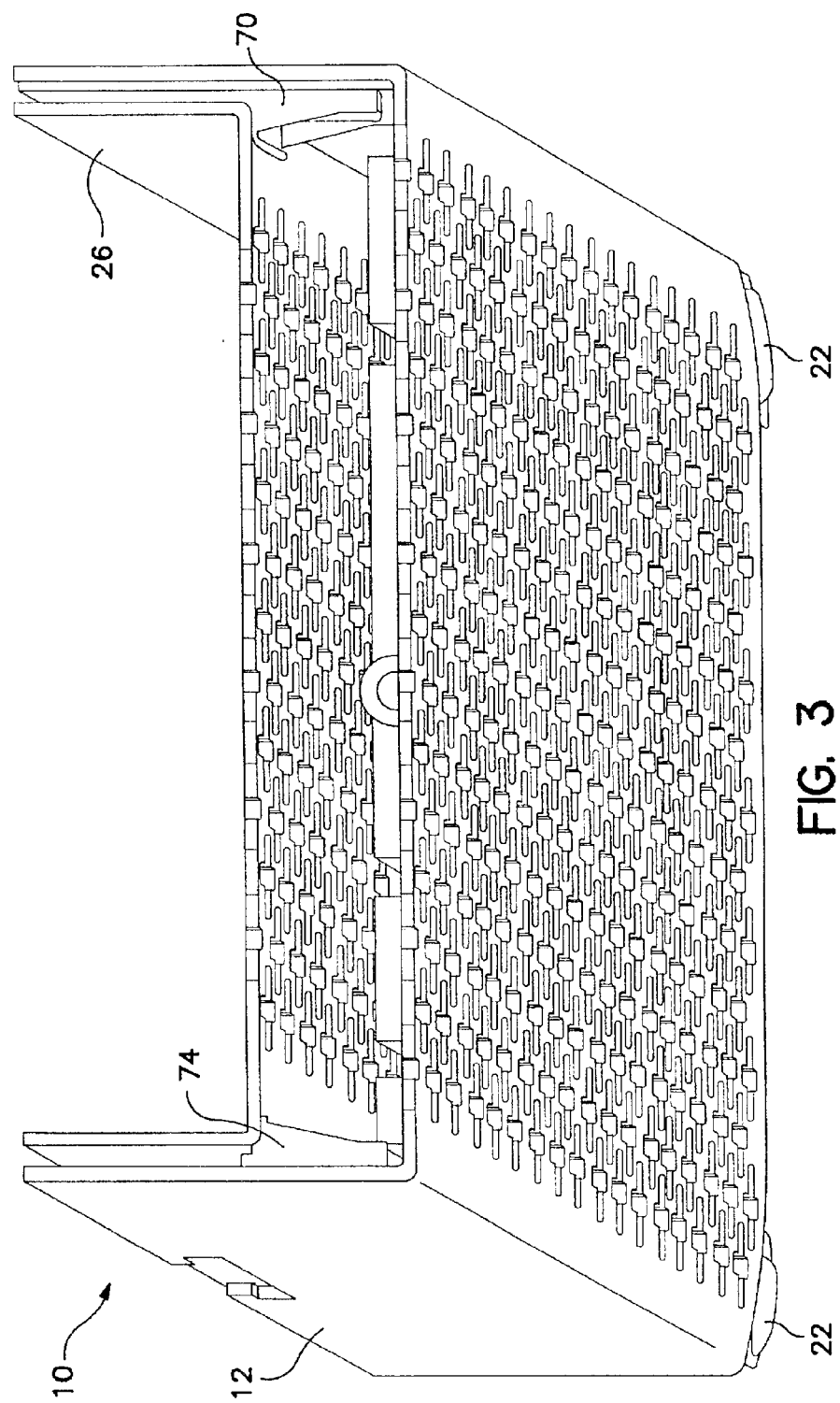
FIG. 3 is a cross-sectional perspective view of a sterilization tray system of the present invention taken along III—III of FIG. 2, and showing a sterilization tray and case assembled together in accordance with the present invention.

Referring to FIGS. 1–3 of the drawings, a tray system in accordance with the present invention comprises a rigid, generally box-like outer case 10 having a pair of side walls 12, 14, a pair of end walls 16, 18 and a bottom wall 20 defining a generally rectangular interior space. Preferably, case 10 is provided with integral feet 22 so that the case bottom wall 20 is spaced above the surface upon which it is placed. Formed in the bottom wall 20 are a plurality of holes 24. Typically, holes 24 are evenly spaced from one another in a plurality of columns and rows. Holes 24 serve the dual purpose of permitting ingress and egress of steam or other sterilant to circulate throughout the case, and also may serve for locating instrument brackets and dividers 25 interiorly of the case. In a preferred embodiment of the invention, holes 24 are formed in a cruciform shaped patterns in accordance with the teachings of copending application Ser. No. 09/312, 126, filed contemporaneously herewith and assigned to the common assignee, Poly Vac, Inc. (Attorney Docket No. Poly Vac 99.02).

The sterilization tray system in accordance with the present invention also includes one or more trays 26, 28 which are sized to fit within case 10. Just as in case 10, the bottom wall 30 of tray 26 and bottom wall 32 to tray 28 include columns and rows of cruciform shaped pattern holes 34, 36, respectively. Tray 26 is supported vertically above bottom wall 20 of case 10 by means of adjustable brackets as will be described in detail hereinafter. Tray 28 rests on top of tray 26. Tray 26 and tray 28 are both provided with integral legs 38 and 40, respectively. Legs 38 and 40 are located slightly inwardly, by the wall thickness of trays 26 and 28 so as to locate one tray stacked on top of the other.

The tray system also includes a removable top 42. Top 42 has a peripheral downwardly depending skirt 44 arranged to engage over the top rim of case 10. Top 42 includes a pair of lifting handles 46 and one or more pairs of locking hinges 48, 50 which may be pivotally or slidably mounted, in known manner, to top 42 for engaging suitably located slots or bosses 52 formed on or in case 10.

Figure 4:
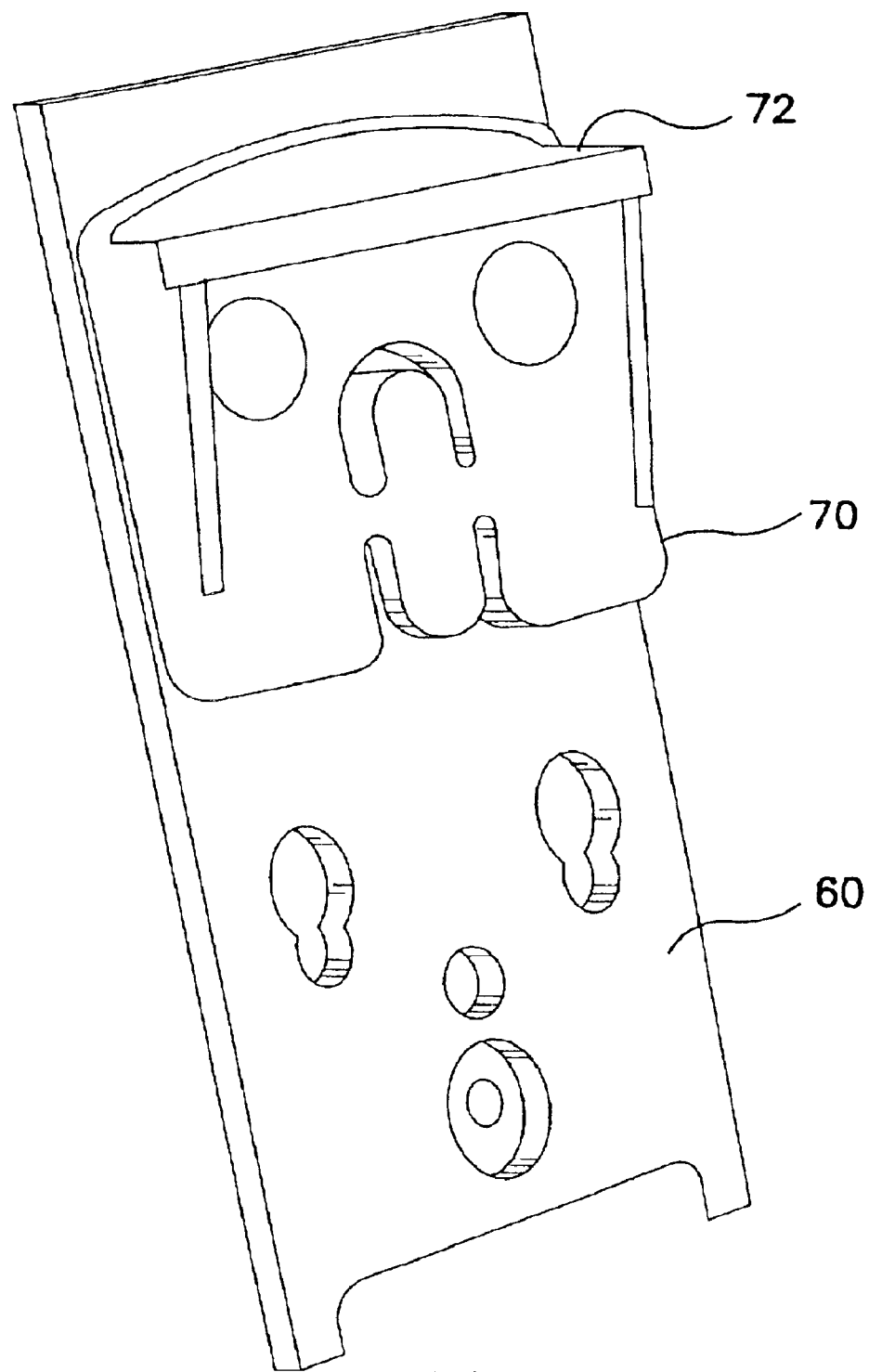
FIG. 4 and FIG. 5 are front and back viewed, respectively, and showing details of a preferred form of vertical adjusting rails in accordance with the present invention.
Figure 5:
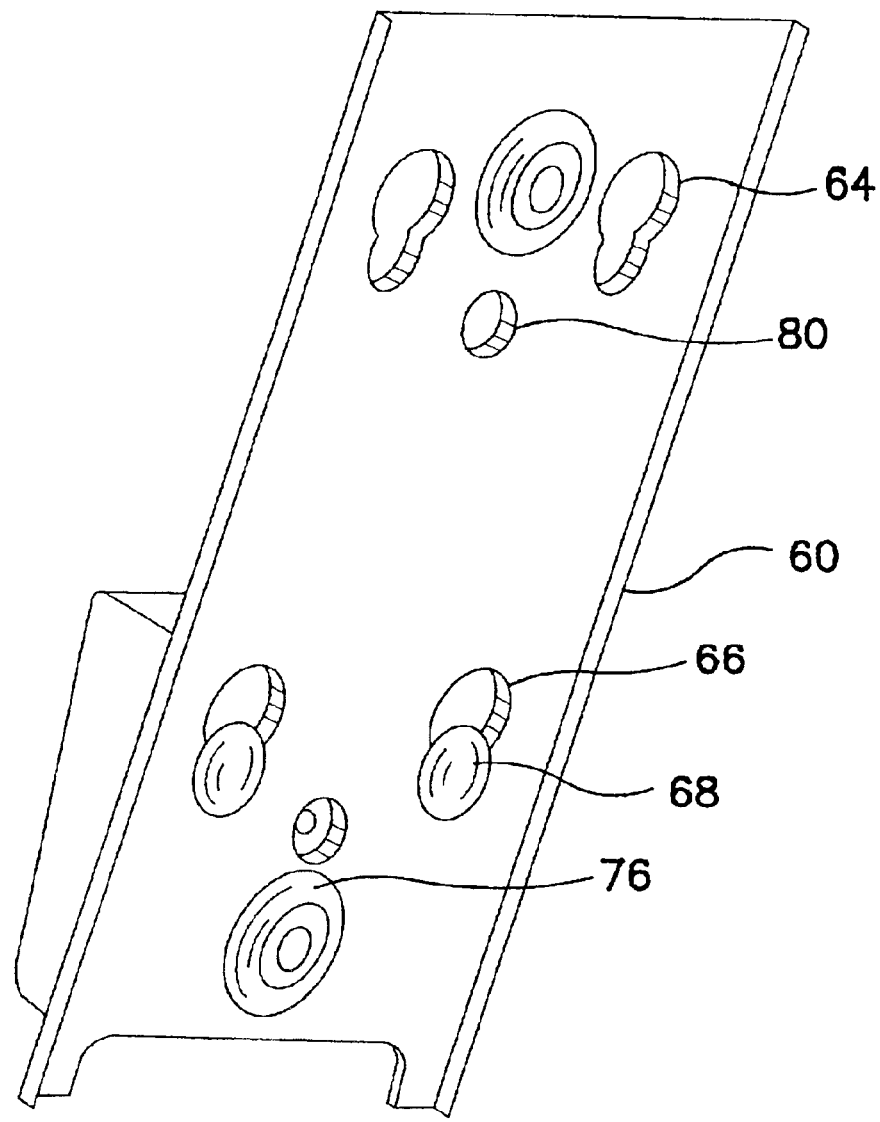
Figure 6:
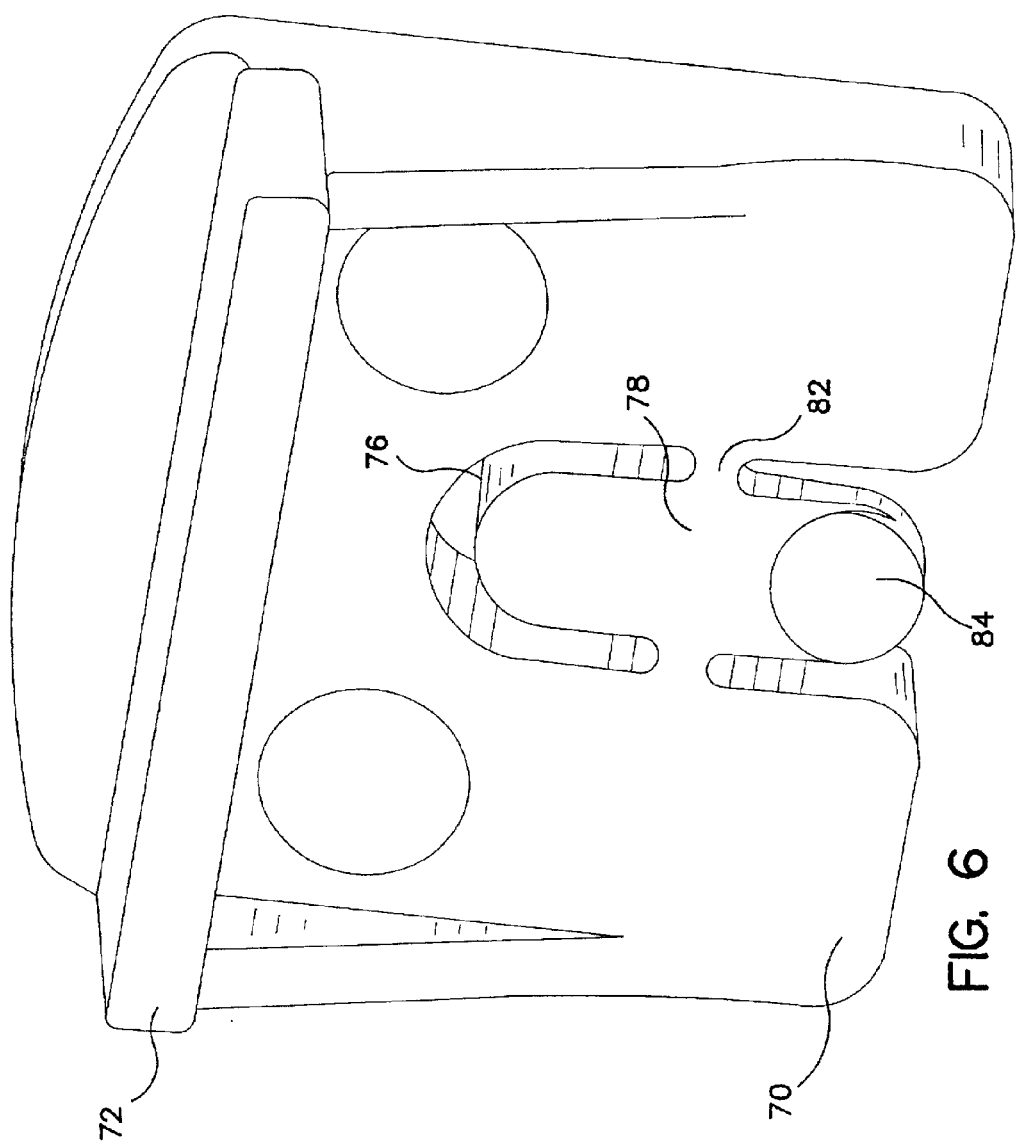
FIG. 6 is an enlarged perspective view showing a preferred form of shelf mounting bracket in accordance with the present invention.
Figure 7:
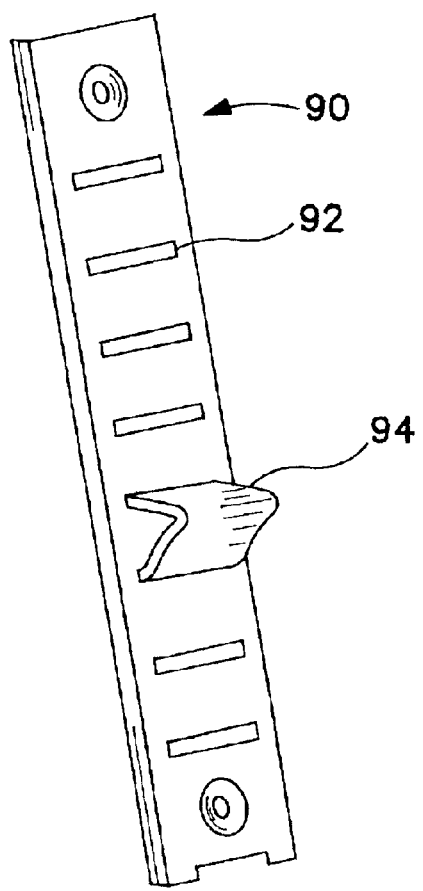
FIGS. 7 and 8 are views similar to FIGS. 4 and 5, respectively, and showing details of an alternative form of vertical adjusting rails in accordance with the present invention.
Figure 8:
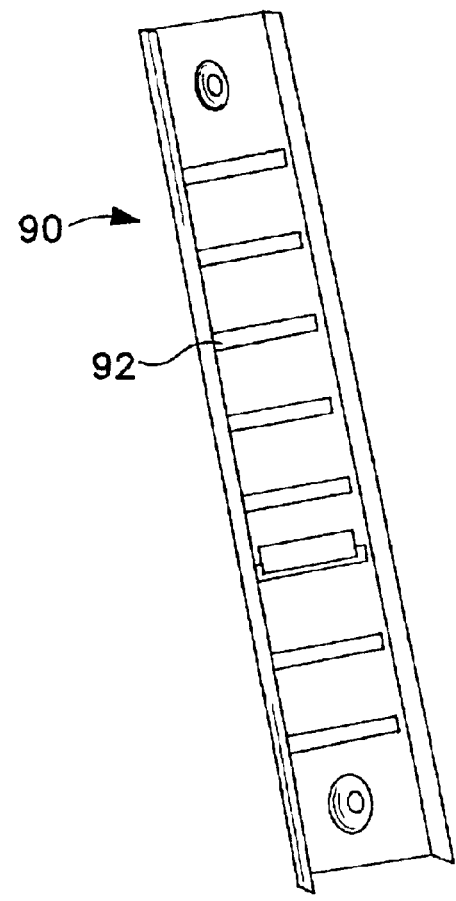

Referring also to FIGS. 4, 5 and 6, a feature and advantage of the present invention is to permit the stacking of one or more trays at selected vertical locations within the case. In order to accomplish this, a plurality of standards 60 are affixed to the case side and/or end walls of case 10. Preferably, but not necessarily, standards 60 are affixed in pairs opposite one another to the case side and/or end walls, i.e. as shown in FIG. 2. Standards 60 preferably are permanently affixed to the case side and/or end walls by means of mechanical fasteners such as rivets 62. Standards 60 include one or more vertically spaced locating holes 64, 66 for accommodating tabs or bosses 68 extending from the backside of shelf or tray brackets 70. In a preferred embodiment of the invention, standards 60 include two or more pairs of vertically spaced keyhole shaped holes 64, 66, while tabs or bosses 68 comprise button-shaped posts extending on reduced diameter stems from the back of each bracket 70. Bracket 70 also includes a shelf 72 for engaging with slots 74 formed in the bottom walls of the trays.

Preferably, and in order to lock brackets 70 on standards 60, brackets 70 include an engageable boss or tab 76 which is mounted on the backside of a pivotally mounted arm 78, for engaging in a hole 80 which preferably is located centrally and slightly below hole pairs 64 and 66. Arm 78 is integral with said bracket, and is made somewhat thinner than the main body of bracket 70, and is joined to the main body of bracket 70 by reduced thickness webs 82. Accordingly, by pressing down on the distal end 84 of arm 72, boss 76 may be pivotally lifted out of engagement with hole 80 in standard 60. This arrangement permits the user to change the vertical position of bracket 70 without using a tool, and without any loose parts. Thus, bracket 70 serves the dual purpose of permitting vertical adjustment of a tray within case 10, and also serves to locate and space a tray within case 10 spaced from the inner walls of the case (see FIG. 3), so as to permit circulation of steam or sterilant within the case, and also avoid trapping of condensation between the inner wall of case 10 and the outer wall of tray 26.

The invention is susceptible to modification. For example, four pairs of standards 60 may be affixed spaced along walls of case 10 for accommodating two trays each occupying substantially one-half the length of the case. Or, six pairs of standards 60 may be spaced for accommodating trays each occupying substantially one-third the length of the case, or one tray occupying approximately two-thirds the length and at tray occupying one-third the length. Alternatively, two or more pairs of standards 60 may be affixed to the end walls of the case for accommodating long, narrow width trays, occupying, for example, one half the width of the case (four standards), one third the width of the length (six standards) or a combination of trays including one occupying substantially two-thirds the width of the case and one occupying substantially one-third the width of the case.

Yet other possibilities are possible. For example, the standards may comprise elongate vertically mounted standards 90 including a plurality of horizontal slots 92 in which are mounted spring clips 94, i.e. similar to conventional bookcase shelf brackets. Still other changes are possible without departing from the spirit and scope of the invention. It is also to be understood that the following claims are intended to cover all of the generic and specific features of the inventions described herein.

What is claimed is:

1. A modular sterilization tray system for medical instruments comprising:
    a rigid, substantially rectangular case having a pair of opposite side walls, a pair of opposite end walls and a bottom defining a generally rectangular interior space;
    a plurality of pairs of standards affixed vertically to at least one of said opposite side walls, and said opposite end walls, said standards having a plurality of vertically spaced holes formed therethrough;
    at least one rectilinear tray for placement in said case, said tray having a bottom; and
    a plurality of brackets for positioning in said holes in said standards for fixing the position of said at least one rectilinear tray at selected elevations of said case, said bracket including a boss formed integrally with the bracket, said boss attached to said bracket by reduced thickness webs.

2. The system of claim 1, further comprising a removable cover.

3. The system of claim 1, wherein at least one of said bottom of said case and said bottom of said tray include a plurality of cruciform shaped openings.

4. The system of claim 3, wherein said openings are configured to accommodate removable instrument brackets and dividers.

5. The system of claim 1, wherein said tray include slots formed on said bottom for positioning said tray on at least one of said plurality of brackets.

6. The system of claim 1, wherein said pairs of standards are affixed opposite one another on at least one of said opposite side walls and said opposite end walls.

7. A bracket for fixing a position of a tray in a modular sterilization tray system having vertically spaced holes therein, comprising:
    a bracket body;
    an engageable boss;
    an arm pivotally attached to said bracket body, said engageable boss mounted on said arm.

8. The bracket of claim 7, wherein said arm includes a backside, a distal end and an opposite end, said engageable boss being mounted on said backside proximate said opposite end.

9. The bracket of claim 8, wherein said engageable boss is configured to engage at least one of the vertically spaced holes of the modular sterilization tray system, said arm being configured to lift said engageable boss from a vertically spaced hole of the modular sterilization tray system by pressing on said distal end.

10. The bracket of claim 7, wherein said arm is integral with said bracket body, said arm being thinner than said bracket body and attached thereto by reduced thickness webs.

11. The bracket of claim 7, wherein said boss is a button-shaped post extended on a reduced diameter stem.

12. A modular sterilization tray system for medical instruments comprising:
- a rigid, substantially rectangular case having a pair of opposite side walls, a pair of opposite end walls and a bottom wall defining a generally rectangular interior space;
- pairs of standards affixed vertically to at least one of said opposite side walls and said opposite end walls, said standards having a plurality of vertically spaced holes formed therethrough;
- at least one rectilinear tray for placement in said case; and
- a plurality of spring clips for positioning in said holes in said standards for fixing the position of said at least one rectilinear tray at selected elevations of said case.

* * * * *